United States Patent [19]
Briggs et al.

[11] 4,019,995
[45] Apr. 26, 1977

[54] LIGNOSULFONATE COMPOSITION AND PROCESS FOR ITS PREPARATION

[75] Inventors: William Scott Briggs, Bellingham; Niels J. Kjargaard, Oak Harbor, both of Wash.

[73] Assignee: Georgia-Pacific Corporation, Portland, Oreg.

[22] Filed: Nov. 7, 1975

[21] Appl. No.: 630,071

Related U.S. Application Data

[63] Continuation-in-part of Ser. No. 439,579, Feb. 4, 1974, abandoned.

[52] U.S. Cl. .......................... 252/62.53; 252/62.52
[51] Int. Cl.² ..................... G01N 27/82; H01F 1/00
[58] Field of Search ......... 252/62.51, 62.52, 62.53, 252/62.54

[56] References Cited
UNITED STATES PATENTS

| | | | |
|---|---|---|---|
| 2,304,308 | 12/1942 | Hurd | 106/308 S |
| 2,933,452 | 4/1960 | Byrd | 252/353 |
| 3,278,425 | 10/1966 | King et al. | 260/124 R |
| 3,344,063 | 9/1967 | Stratton | 260/439 R |
| 3,546,197 | 12/1970 | Benko | 260/124 |
| 3,766,229 | 10/1973 | Turner et al. | 260/429 K |

*Primary Examiner*—F.C. Edmundson
*Attorney, Agent, or Firm*—Peter P. Chevis

[57] ABSTRACT

Lignosulfonate and sulfonated tannin compositions having magnetic properties which may be water soluble and a process for their preparation are described.

31 Claims, No Drawings

LIGNOSULFONATE COMPOSITION AND PROCESS FOR ITS PREPARATION

This application is a continuation-in-part of U.S. Pat. application Ser. No. 439,579, filed on Feb. 4, 1974, now abandoned.

The invention pertains to lignosulfonate and sulfonated tannin compositions and a process for their preparation. More particularly it pertains to an iron lignosulfonate composition having ferromagnetic properties.

BACKGROUND OF THE INVENTION

Lignin is a polymeric substance found in plant and vegetable tissue associated with cellulose and other plant constituents. In the pulp and paper industry, lignin-containing material such as wood, straw, corn stalks, bagasse, and other vegetable and plant tissues are processed to recover the cellulose or pulp with the lignin usually being sulfonated or chemically modified in some other way and obtained as a by-product in large quantities. Sulfonated lignin or lignosulfonates and sulfonated tannins have been mainly used as dispersants and for other uses utilizing the surface-active properties of the products. There are numerous disclosures for the preparation of iron and other metal lignosulfonate salts which basically involve the intermixing of metal salt with spent sulfite liquor and digesting mixture under acid conditions to replace the cation associated with the sulfonate groups of the liquor with the desired metal. For example, in U.S. Pat. No. 2,935,473, the preparation of iron, chromium, aluminum, and lignosulfonate salts is disclosed for use as thinners in drillings fluids. Lignosulfonates and sulfonated tannins are also complexing agents and trace metal compositions of these sulfonated products have been used as micronutrients alone or added to mixed fertilizers to supply trace elements to plants. In U.S. Pat. No. 3,244,505, preparation of lignosulfonate micronutrient products is disclosed, including the preparation of iron lignosulfonates and other trace metal lignosulfonates with metal contents in excess of the stoichiometric amount of metal to react with the sulfonate groups on the lignosulfonate. Also the reaction of aluminum and iron basic salts with lignosulfonate for the precipitation and recovery of lignosulfonate from spent sulfite liquor is disclosed in U.S. Pat. No. 3,270,001.

The technological advances made in the last few years have greatly increased the demand for magnetic materials. These advances have also created needs for magnetic material of unique properties. Ferromagnetism heretofore has been associated only with the solid state where the existence of interatomic exchange forces is possible. Typical ferromagnetic solids such as metals, metal oxides, and alloys are by nature water-insoluble and considerable processing may be required to obtain such materials in the quasi-fluidic form which is necessary for certain applications, e.g., see U.S. Pat. Nos. 3,351,413; 3,620,584; and 3,635,819. An organically-based ferromagnetic composition which could be made in water-soluble form or not, as desired, would not only simplify the application to practice of several uses proposed for such ferromagnetic quasi-fluids but also increase the scope of usage of such products.

It is, therefore, an object of this invention to provide an organic composition having ferromagnetic properties. A further object is to provide a lignosulfonate magnetic composition. A still further object is to provide a water-soluble lignosulfonate or sulfonated tannin composition having ferromagnetic properties and a process for its preparation.

The above and other objects may be attained according to a preferred embodiment of this invention by reacting an iron compound and a purified lignosulfonate or sulfonated tannin material in an aqueous medium at a temperature preferably of from about 40° to 230° C maintained at a pH of at least 5.5 in a manner which permits the formation of magnetite or other magnetic oxide of iron or other magnetic iron composition, e.g., by causing change in the oxidation level of the iron to obtain the iron in the ferrous and ferric states under conditions for the formation of magnetite or other magnetic iron oxide or oxyhydroxide in an aqueous medium.

The term "ferromagnetic," as used herein, means being magnetic in a high degree like iron, coablt, or nickel. Theoretically, magnetism of matter results from orientation and alignment of the magnetic moments of electrons. Recently various classifications have been made in order to categorize subtle differences in magnetic behavior or electronic orientation as may be noted in relatively recently published texts as "Magnetism and Metallurgy," Vol. 1, edited by A. E. Berkowitz et al and published by Academic Press, New York, (1969) or the general review of Kirk-Othmer Encyclopedia of Chemical Technology, 2nd Edition, Vol. 12, published by Interscience Publishers. Two examples of these classifications for strongly magnetic materials, in addition to ferromagnetism, are ferrimagnetism and superparamagnetism. Ferrimagnetic refers to chemical compounds in which the magnetic moments of the atoms which contribute to the magnetic properties are partially canceled by the magnetic moments of adjacent atoms. The term superaramagnetic is applied to chemical compositions which are normally ferromagnetic in the bulk state but which exhibit slightly different properties after having been subdivided to the point where an individual particle is a single magnetic domain. For practical purposes and for uses for which the materials of this invention are to be used, the interatomic relationships which result in the magnetism are of little importance. The attractive force, as referred to herein is relative magnetic susceptibility, is the main magnetic property of importance. Thus, the term, ferromagnetic, is used herein to mean materials which are attracted to a magnet to a high degree, regardless of the interatomic relationships or other properties which, at times, may be associated with ferromagnetism. The materials of the invention appear to have properties similar to those associated with ferromagnetic materials in fine particle size and are referred to as ferromagnetic when the material is attracted to a magnet with a significant force as compared to substantially pure iron, i.e. having a relative magnetic susceptibility or a magnetization, based upon the iron content, of at least 60 percent of substantially pure iron, when measured in a magnetic field of about 240 oersteds in the manner described in the examples below. The magnetization or magnetic susceptibility of substantially pure iron when determined under the above conditions is about 2 grams per gram of iron.

While the invention will be described mainly in reference to use of lignosulfonate in the preparation of the magnetic compositions, the procedures and conditions are also applicable to sulfonated tannin. Tannin as found in tree bark, or tannin extracts such as quebraco, wattle, and myrobalan, and others may be sulfonated in a manner similar to that employed in sulfonation of wood in pulping to obtain water-soluble products having properties similar to sulfonated lignin in preparation of the magnetic composition.

In carrying out the reaction under above conditions, particular iron-lignosulfonate or sulfonated tannin compositions are obtained which are generally water-soluble and may have magnetic susceptibilities on an iron basis above that of magnetite and properties generally associated with ferromagnetic materials in fine particle form. The magnetic susceptibility of the composition, based upon the iron content, is independent of the concentration of the solution. With decrease in temperature from 0° to −66° C, about 10 percent increase in magnetic susceptibility of the composition in dry form is obtained. Furthermore, the magnetic lignosulfonate composition, e.g., when dissolved in water, has the characteristics of a lignosulfonate or a polyelectrolyte solution. No separation of reacted iron from lignosulfonate has been obtained by filtration, centrifugation, by passage through a gel permeation column, or by diffusion into agar gel indicating that the composition is not a dispersion or suspension of a magnetic iron oxide in a lignosulfonate solution. Further, the iron is not present in an ionizable form; nor is the iron present in a manner such that the iron may be removed from the lignosulfonate by use of ion exchange resins or strong chelating agents as is true for the iron lignosulfonate complexes commonly known. The average molecular weight of the composition increases with the amount of iron reacted or present in the composition. For example, when a lignosulfonate having an average molecular weight of about 60,000, as determined by diffusion, is reacted with sufficient iron to obtain about 15 to 18 percent iron in the composition, the composition may have an average molecular weight of over 100,000. Upon reaction with additional iron, the molecular weight will increase still further, indicating that there is some cross-linking being obtained between the lignosulfonate molecules. The amount of iron which can be incorporated into the lignosulfonate also increases with the increase in the sulfonate sulfur content of the lignosulfonate, further indicating some chemical interaction between the lignosulfonate and the iron. X-ray diffraction of the magnetic lignosulfonate composition shows a spectrum similar to that of magnetite or gamma ferric oxide, indicating that the iron may be present in some structural form of iron oxide. a Mossbauer spectrum of the composition exhibits a hyperfine structure in the range of −10 to +10 mm/sec relative to iron metal which is also indicative of an ordered molecular structure of the type associated with ferromagnetic iron oxide.

While the present invention is not to be considered to be based on any particular theory of reaction mechanism, such reaction mechanism not being completely understood, it is believed that a composition is obtained where the iron-oxygen polymeric units are bound in some manner to the lignosulfonate or sulfonated tannin composition. Apparently two reactions are involved in the formation of the magnetic compound. Upon increasing the pH of a solution containing lignosulfonate and the iron compound or compounds to a pH of about 5.5 and above, an initial precipitate is obtained, at least with solutions of higher concentrations. The initial precipitate is believed to be an iron hydroxide or oxyhydroxide material which appears to be associated in some manner with lignosulfonate to a certain extent. Thus, it is believed to be essential that the iron compound be in solution or in contact with the lignosulfonate at a pH at least as high as that at which the precipitate begins to form which will ordinarily be 5.5 or greater. Upon heating the resulting mixture with alkali, alkali is consumed and a composition is obtained which has ferromagnetic properties.

Processes previously used for the preparation of magnetic iron oxides or oxyhydroxides in an aqueous medium are contemplated as useful for the preparation of the magnetic lignosulfonate or sulfonated tannin composition as long as the conditions are not so drastic as to destroy the basic polymeric structure of the lignin or tannin. Addition of the lignosulfonate or sulfonated tannin to the aqueous medium prior to initiating the preparation of such products will result in the combination of the iron oxide with the sulfonated product in the formation of the product of the invention. A convenient method for carrying out the reaction is to dissolve the lignosulfonate, e.g., and a water-soluble iron salt in water, add the alkali to the solution in an amount of about 1 equivalent per equivalent of iron, and react the mixture to convert it to the desired composition. There will usually be a need for a change in the oxidation state of the iron in the presence of the alkali to obtain the iron in both the ferric and ferrous states in the desired proportions, e.g., approximately those present in magnetite. When a ferrous iron compound is used, the reaction of the iron with the lignosulfonate is usually carried out by heating the mixture with agitation in air to oxidize a portion of the iron. During the heating, a greenish-black material is initially obtained. In addition to air, other oxidizing agents known to oxidize ferrous iron under alkaline conditions, such as for example hydrogen peroxide, a halogen as chlorine or bromine, and hypochlorite may be added under controlled conditions to provide the relatively mild oxidizing conditions sufficient to oxidize the ferrous iron without substantial oxidation or degradation of the lignin. When a mixture of ferrous and ferric iron compounds in proportions to obtain magnetite are added to the heated solution at a suitable pH, the oxidation is not necessary and the ferromagnetic composition may be obtained upon heating the mixture with sufficient alkali to form the ferromagnetic lignosulfonate composition.

A ferric iron compound may also be used as the sole iron compound. When this is done, the reaction is carried out under controlled conditions, such as under an inert atmosphere or adding the ferric compound with limited agitation in a manner which will result in some reduction of the ferric compound. Lignosulfonates generally contain some reducing groups which are apparently present in an adequate amount to reduce a sufficient proportion of the ferric compound added to the ferrous state to obtain the desired composition. Also, the reaction with the ferric salt may be carried out by initially subjecting the mixture to reducing conditions to reduce the ferric iron partially or completely to the ferrous state and then carrying out the reaction the same as noted above.

Lignosulfonates or sulfonated lignin obtained from any source may be used in preparation of the magnetic composition. While there is some variation in the chemical structure of lignin and of other constituents found in different plants, depending upon the type of plant, place where grown, and also upon the method used in recovery or isolation of the particular constituents from the plant tissue, the basic structure and properties in lignin upon sulfonation are similar.

One of the main sources of lignosulfonates or sulfonated lignin is the residual pulping liquors obtained in the pulp and paper industry. In the sulfite pulping process, lignocellulosic material is digested with a sulfite or bisulfite. The residual liquor obtained is a sulfonated liquor, commonly referred to as "spent sulfite liquor," containing the sulfonated lignin. In other pulping processes, the residual pulping liquor as obtained may not be a sulfonated product so that the lignin may not be in a sulfonated form. However, the residual liquor or products containing the lignin portion of the lignocellulosic materials from the sulfite or other processes may be sulfonated by various known methods to the degree desired. For example, the residual liquor obtained in an alkaline pulping process such as kraft, soda, or other processes may be sulfonated to sulfonate the lignin, or the lignin may be recovered from the liquors and then sulfonated. Lignin, sulfonated to the extent that the sulfonated lignin contains more than 3 percent sulfonate sulfur, is preferred. In the sulfite pulping process, most of the lignosulfonates obtained in the residual liquor are sulfonated to this extent, usually containing from 4.5 to 6 percent sulfonate sulfur.

Spent sulfite liquor or a product obtained upon sulfonation of a residual pulping liquor generally contains carbohydrates or sugars, degradation products of carbohydrates, and resinous materials as well as other organic and inorganic constituents in addition to the sulfonated lignin. The organic non-lignin constituents, which are usually low molecular weight materials having molecular weights of 400 or less, generally have to be removed. The lignosulfonate must be substantially free of the low molecular weight organics which have multiple coordination sites, such as hydroxyl and carboxyl groups as present in sugars, sugar acids, and sugar degradation products, and of products such as lactone-type wood extractives which, upon hydrolysis under alkaline conditions, form the multiple coordination sites. The presence of these low molecular weight polyhydroxy and polycarboxy, non-lignin constituents interferes or inhibits the reaction resulting in the formation of the magnetic lignosulfonate composition. It is known that iron forms unique complexes with such compositions, for example, sugar and sugar derivatives, which apparently prevent the formation of magnetic iron oxides. The treatment of spent sulfite liquor or a sulfonated residual pulping liquor with an acid, alkali, or an oxidizing agent, as often done to remove or modify some of the non-lignin constituents, is generally not sufficient to purify lignosulfonate for the purposes of this invention. Thus, even if the liquors have been subjected to such treatment for purposes of treating the lignin of non-lignin constituents, generally additional processing must be used to further inactivate or remove the organic, non-lignin constituents to render the lignosulfonate sufficiently free of these impurities to keep from inhibiting the formation of the magnetic lignosulfonate compositions according to this invention. Physical separation methods, such as dialysis and gel permeation, may be conveniently used to obtain adequate purification. However, known chemical methods, such as amine, acid, or calcium hydroxide precipitation, may also be employed. The interfering constituents may also be made ineffective or removed from spent sulfite liquor by prereaction of the liquor with an iron compound. For example, the iron compound may be dissolved in a dilute liquor containing up to about 4 weight percent spent sulfite liquor solids and heated with alkali under the conditions required for forming a magnetic product, but no such product forms. After filtration and repeating the reaction with further additions of iron and alkali, the remaining solution reacts to form a magnetic composition.

The lignosulfonate or sulfonated lignin does not have to be entirely free of the organic non-lignin constituents. However, the amount of sugars or carbohydrates and other non-lignin organic constituents in the lignosulfonate is generally maintained to less than about 5 weight percent, with the concentration of the sugar carboxylic acids, the more detrimental constituents, being generally maintained to 2 percent or less. The inorganic constituents found in these liquors are not necessarily detrimental in themselves other than serving as diluents. Thus, the terms "lignosulfonate" and "sulfonated lignin" as used herein mean the sulfonated lignin chemical itself, and the term "substantially free" of the low molecular weight, organic, non-lignin constituents means sufficiently free of these constituents to keep these constituents from seriously inhibiting or reacting to form products which will seriously inhibit the formation of the magnetic iron oxide and the resulting magnetic lignosulfonate composition. Products obtained upon sulfonation of bark or the tannin extract will likewise contain in addition to sulfonated tannin low molecular weight organics which must be removed prior to formation of the magnetic compositions. The procedures and method described for separation or recovery of lignosulfonate from spent sulfite liquor are applicable for recovery and purification of the sulfonated tannins. Thus, the term "sulfonated tannin" as used herein means the sulfonated tannin itself substantially free of the low molecular weight, organic constituents which inhibit the formation of the magnetic oxide. Given the teaching of the present invention, only routine experimentation will be required to determine the degree of purification necessary for a given sulfonated lignin or tannin containing material to obtain a product having the desired properties in a given reaction with an iron compound.

The lignosulfonate in spent sulfite liquor or as obtained upon the sulfonation of a pulping liquor may be a sodium, magnesium, calcium, or ammonium salt, depending upon the base which was used in the pulping or sulfonating process. The lignosulfonate or sulfonated tannin as the acid or a salt of any of the above cations or of other metals may be used. Salts of metal ions known to cross-link with lignosulfonates or sulfonated tannins, such as chromium, may also be used, but due to the additional cross-linking, a water-soluble ferromagnetic composition of iron-chromium lignosulfonate may be obtained, unless a low molecular weight lignosulfonate is used in the reaction. Also, lignosulfonate salts of amines, such as triamylamine and other amines which are used in the recovery of lignosulfonate from spent sulfite liquor and other mixtures by precipitation or extraction of the lignosulfonate as the amine salt, may be employed. Some of the amine salts are insoluble but upon addition of sufficient alkali, the amine is regenerated and the lignosulfonate is converted to the salt of the alkali to provide the required solubility. The presence of the amine in the reaction mixture does not materially affect the reaction. Likewise, lignosulfonates of different molecular weights may be used as long as the lignosulfonate has the required solubility.

The concentration of the lignosulfonate or sulfonated tannin in the solution used in the reaction may be widely varied from practically zero to over 30 weight percent with a practical concentration being in the range of ½ to 20 weight percent. Preferably the concentration is in the range of 3 to 10 percent, permitting the lignosulfonate solution obtained upon fractionation of recovery of the lignosulfonate from a pulping liquor by dialysis or gel permeation to be used directly. At the higher concentrations, the viscosity of the reaction mixture increases rapidly with the increase in concentration, especially over 30 weight percent, making it more difficult to handle and react. The more dilute solutions are also preferably used with large additions of iron, since this reduces the tendency of "salting out".

To obtain compositions having magnetic properties, the amount of iron which must be added to the aqueous medium with the lignosulfonate or sulfonated tannin is at least about twice the stoichiometric amount of iron, expressed as ferric iron, necessary for reaction with the sulfonate groups on the lignosulfonate or sulfonated tannin for simple salt formation. This large excess of iron is necessary, otherwise the ordinary salt-type metal complex is obtained. For the commonly available lignosulfonate, this amount of iron is about 9 percent, which when reacted gives products containing about 8 percent iron. Products containing less iron having some magnetic properties may be obtained as the result of incomplete reaction. The magnetic strengths based upon the iron content do not vary greatly with products with contain from about 9 to 18 percent of iron. Apparently at these levels for products containing from 5 to 6 percent sulfonate sulfur, most of the iron is associated with the lignosulfonate in the magnetic or stable form, with only a small amount of the iron being present in a form such as an ionizable cation of a salt. Less than about 0.5 percent of iron is ion exchanged by treatment with cation ion exchange resins. Generally the iron compound is added in a sufficient amount to supply about 10 percent of iron and preferably to supply from 20 to 50 weight percent of iron, based upon the lignosulfonate. The amount of iron which can be combined with the lignosulfonate or sulfonated tannin increases with the sulfonate sulfur content of the lignosulfonate or sulfonated tannin and reaches a limit regardless of the excess amount of iron added. With lignosulfonates containing from 5 to 6 weight percent sulfonate sulfur, up to about 35 percent iron may be bound, while for a lignosulfonate containing eight percent sulfonate sulfur, the iron content can be increased to about 45 weight percent. Compositions containing from about 18 and above percent iron are preferred. When products are prepared with relatively high concentrations of iron, somewhat more dilute lignosulfonate solutions may be preferably used to prevent salting out. The reaction may also be carried out at the higher concentrations with the iron and alkali being added continuously or in more than one step. For example, a lignosulfonate solution containing about 3 to 10 percent lignosulfonate may be used to which a sufficient amount of an iron salt, for example ferrous sulfate, may be added to provide a product containing up to about 20 percent or iron. After the addition of the ferrous salt to the solution, the alkali would be added to the solution to increase the pH to the desired level and then the product heated until substantially all of the iron is converted to a magnetic iron oxide and bound with the lignosulfonate to form a water-soluble composition. To this mixture an additional amount of the iron salt is added and the process repeated. By this procedure, products containing over 30 percent iron may be prepared without having to use more dilute solutions or work with mixtures of high viscosity which would be normally obtained by the addition of the relatively large amount of the iron compound and alkali to the solution. The above procedures may also be used with the more concentrated lignosulfonate solutions even at lower levels of iron addition to minimize the viscosity problem.

Any iron compound which is soluble in water under acidic conditions and forms iron hydroxide upon addition of alkali may be used in the reaction with the lignosulfonate or sulfonated tannin to form the ferromagnetic composition. Inorganic salts, such as chlorides, bromides, nitrates, and sulfates are preferred. However, organic iron compounds such as the formates or acetates may also be used. These compounds may be dissolved in water prior to addition to the lignosulfonate or sulfonated tannin solution or may be added directly to the solution. The method of forming the iron compound and the lignosulfonate solution may vary as long as the iron is in contact with the lignosulfonate at the time the desired pH is obtained. This can be generally accomplished by intermixing the iron compound with the lignosulfonate before the addition of the alkali or the alkali can be added to the lignosulfonate solution prior to the addition of the iron compound. In these situations, the proper pH conditions are obtained to effect the precipitation. The same result is obtained when the iron compound in the dry state is added to the lignosulfonate solution. It is not necessary to use an iron compound which is completely soluble in water or in the lignosulfonate solution. However, the compound must be at least partially soluble to supply sufficient iron ions to initiate the reaction which would then permit additional iron to dissolve and react.

There appears to be a definite ratio of alkali, based upon the amount of iron added, utilized in the formation of the magnetic composition. Although products with significant magnetic susceptibility and yield may be obtained by reacting one third equivalent or less of alkali per equivalent of iron, about 1 equivalent of alkali per equivalent of iron is preferred in the reaction to combine most of the iron added with the lignosulfonate or sulfonated tannin in magnetic form. With smaller amounts of caustic or alkali, the yield of the magnetic composition as well as the iron content obtained in the product decreases. For example, if about one half equivalent of alkali per equivalent of iron is added, the amount of iron associated with the lignin may be about half of that which would be obtained if the iron compound and lignosulfonate were reacted with 1 equivalent or a sufficient amount of alkali for conversion of all of the iron to ferrous hydroxide. Generally, the amount of the alkali added is in the range of about 0.9 to 1.5 equivalents of alkali per equivalent of iron, preferably from 1.1 to 1.25 equivalents. With a small excess over one equivalent, a sufficient amount of alkali is present to neutralize or bring the reaction mixture to a desired pH and still have about one equivalent of alkali available for reaction. No particular advantage is gained in using an excess of alkali over about 1.5 equivalents. Large excesses of alkali, such as for example caustic in an amount of from 2 to 2.5 equivalents per equivalent of iron, should be avoided. Above pH 13, lignosulfonate may undergo sufficient hydrolysis and degradation, is heated for an appreciable length of time, to materially alter its properties. The reaction mixture containing the iron salt displays considerable buffering action in the pH range of from about 7 to 8.5. For example, generally a relatively small amount of caustic, less than one third equivalent per equivalent of iron, is necessary to bring the reaction mixture from about pH 4 to a pH of about 7, but thereafter 0.75 equivalents or more of caustic per equivalent of iron may have to be added to increase the pH to about 8.5. Normally, upon addition of about 1.1 to 1.25 equivalents of caustic to the reaction mixture, the pH initially may be in the range of 10 to 11 and an alkali will start to be consumed immediately upon addition. As the reaction proceeds, the pH continues to decrease so that at the end of the reaction the pH will be usually in the range of 6.5 to 8. Will smaller amounts of caustic, the initial and final pH's will be lower. The amount of caustic consumed in the reaction to substantially associate all of the iron does not vary greatly whether the alkali is added all at once or added continuously to provide the necessary presence of alkali and maintain the reaction mixture at the desired pH of at least about 5.5. However, when the reaction is carried out at a constant pH, it is generally carried out at a pH of at least 6, preferably at a pH in the range of 7 to 10.

Any alkali which will provide hydroxide groups without insolubilizing the lignosulfonate or sulfonated tannin may be used in the reaction with the iron and lignosulfonate or sulfonated tannin, with the hydroxides and oxides of alkali metals, such as sodium, potassium, and lithium being preferred. Sodium hydroxide is most often employed due to its cost and availability. Ammonium hydroxide and organic hydroxides, such as tetramethylammonium hydroxide, may also be used. In addition, alkaline earth metal hydroxides and oxides, such as calcium and magnesium hydroxide, may be employed. It is known that the addition of alkaline earth hydroxide to a lignosulfonate solution may result in the insolubilization of the sulfonated lignin. When the alkaline earth metal hydroxides are used, they are added slowly or periodically to keep the pH below the precipitation point of the lignosulfonate, preferably at a pH of 7 or so. In the presence of alkali metal hydroxides, the characteristics of the lignosulfonate are changed such that the precipitation normally obtained with the alkaline earth hydroxide is not obtained. Thus, mixtures of sodium or potassium hydroxide with calcium or magnesium hydroxide may be generally employed under most conditions without precipitation of the lignin.

The temperature at which the iron compound and lignosulfonate are mixed and at which the pH adjustment is made is immaterial and may be widely varied from below room temperature to the temperature used for reacting the mixture. However, when using the preferred embodiment of the invention to obtain the ferromagnetic composition, the lignosulfonate and iron mixture should be preferably heated with the alkali at a temperature of at least 40° C and, generally, a temperature of at least 80° C is used to obtain a more rapid reaction rate. At lower reaction temperatures, the rate of reaction or the formation of the ferromagnetic material is relatively slow which likewise requires controlling the rate of oxidation or reduction of the iron in the mixture to correspond to this rate to have the change in oxidation state of the iron extend over most of the reaction period. A reaction temperature in the range of 90° to 140° C is preferred. At the preferred temperatures, a reaction time in the range of from 15 minutes to 4 hours may be generally sufficient to substantialy combine all of the iron in the magnetic form for the mixture concentrations normaly used. For the more concentrated, highly viscous solutions or reaction mixtures, longer times may be required which may be extended, for example, to 24 or more hours at these temperatures without deleterious effect. While a higher temperature may have no particular disadvantages, the reaction may be most conveniently carried out in about 1 to 4 hours at temperatures of from 90° to 100° C without the use of pressure equipment. At these temperatures, the rate of reaction is sufficiently rapid to correspond favorably to the rate of oxidation which can be obtained from ferrous to ferric iron by relatively mild agitation of the reaction mixture in air. However, temperatures from room temperature or below up to 230° C and higher may be employed as long as the reaction mixture is not maintained at these higher temperatures for extended periods of time resulting in the degradation of the lignosulfonate and insolubilization of the mixture. The rate of reaction increases with temperature so that with reaction temperatures of 200° C and above, just heating of the mixture to that temperature may be sufficient to substantially complete the reaction, while at 25° to 40° C from 12 to 48 hours may be required.

Generally, after the completion of the reaction, the reaction mixture is cooled and preferably processed further by known methods to separate the magnetic lignosulfonate composition from the inorganic salts or other impurities which may be present. At this point the reaction mixture is filtered to remove, if not already removed, the calcium sulfate which may be present if a calcium lignosulfonate sulfate were used as reactants. In addition to the insoluble calcium sulfate, the reaction mixture may contain soluble inorganic salts which have a diluent effect, such as salts of the cations of the alkali and anions of the iron compound. These salts and other low molecular constituents may be conveniently removed by use of dialysis or other physical separation methods such as gel permeation. After the removal of the inorganic salts, the solution containing the magnetic composition may be evaporated and dried, using accepted methods. Once the composition has been formed, it is stable in presence of alkali and acids at pH's in the range of 1 to 13 without decomposition. The composition obtained is ferromagnetic in solution as well as when dried. The composition may be dried and redissolved in water numerous times without significantly affecting the magnetic susceptibility of the product. Compositions containing more limited amount of iron may also be dissolved in organic solvents such as dimethylsulfoxide and dimethylformamide by converting the composition to an amine salt such as a pyridinium salt.

The ferromagnetic iron composition may be used in the dry form or as an aqueous solution. In the dried form, the product may be pressed with a binder to form magnetic bodies of different shapes and used to replace iron oxide and other magnetic materials in certain applications. The product may also be used in magnetic weaving, magneto location, and for other purposes where the water-solubility of the composition is desirable. The water-solubiltiy of the composition also greatly simplifies its use in material separation processes, such as in ore flotations, where separation are enhanced by magnectically-induced variations of apparent fluid weight. The composition also may be used in phase separation such as those of liquid extraction processes where the partitioning of the phase may be magnetically improved.

Where desired, a water soluble product produced according to this invention may be rendered water insoluble by causing the product to undergo a suitable reaction for rendering lignosulfate materials water insoluble, e.g., reaction with a phenol-formaldehyde resin.

In addition to using iron only, other polyvalent metals such as nickel, manganese, and other metals known to form ferrites or magnetic oxy or hydroxy compounds with iron may be used in combination with the iron. The metal compound with the iron compound may be added to the lignosulfonate solution in proper proportions for the formation of the ferrite or desired composition and reacted in a manner similar to that when iron is used alone, with some adjustments being made to obtain the optimum formation of the respective metal oxide for the formation of the ferrite or magnetic composition.

The following examples further illustrate the invention.

EXAMPLE I

A number of ferromagnetic compositions were prepared with different iron contents. The lignosulfonate used for the reaction was obtained from a fermented calcium-base spent sulfite liquor which was fractionated by gel permeation to remove the carbohydrates or sugars and sugar degradation products and other non-lignin constituents from the liquor. The lignosulfonate was the high molecular weight portion of the liquor and represented about a 30 weight percent fraction of the liquor solids. After fractionation, the lignosulfonate fraction was sprayed-dried. The weight average molecular weight of the lignosulfonate was about 25,000 as determined by the agar gel method as described in the J. Amer. Chem. Soc., Vol. 81, 2045 (1959) by J. Moacanin et al. It had a sulfonate content of 5.6 weight percent as determined by the method described in Analytical Chemistry, Vol. 32, 850 (1960) by Fred R. Folely and Luella H. Johnson.

In 150 milliliters of distilled water, 10 grams of the lignosulfonate were dissolved to give a solution containing about 6.3 weight percent of lignosulfonate. To this solution, 5 grams of ferrous sulfate heptahydrate were added which supplied about 1 gram of iron. After the iron compound was dissolved in the lignosulfonate solution, 6 milliliters of 6.2N sodium hydroxide were added which increased the pH of the mixture to about 10. The mixture was reacted in an open vessel at a temperature between 90° to 95° C by being placed in a steam bath for 2 hours and continually stirred. After the reaction, the mixture was allowed to cool to room temperature, filtered to remove calcium sulfate, and then dialyzed in a regenerated cellulose casing against running tap water for 72 hours. The dialyzate, the fraction remaining in the casing, thus obtained was then air-dried, ground, and analyzed for iron content. The final product had an iron content of 9.0 weight percent on an air-dried basis.

The relative magnetic susceptibility of the above product and products in the other examples was determined using a procedure similar to that described by D. F. Evans in the Journal of Chemical Society (A), London, 1967, 1670. In the procedure, two similar magnets were fixed in position on the pan of an analytical balance with the north pole of one of the magnets facing the south pole of the other. The pole faces of each of the magnets were square having a dimension of 2.5 cm on edge. The magnets were placed with a pole gap of 3.3 cm at the bottom and 3.5 cm at the top. In determining the magnetic susceptibility, the sample was ground into a fine uniform powder and packed into a Pyrex test tube of the type normally used for nuclear magnetic resonance measurements having an inside diameter of 4 mm. The sample tube was rigidly fixed between and near the top of the two magnets so that the top of the sample in the test tube was about 5 mm below the top of the magnets. The relative magnetic susceptibility was obtained by noting the change in weight of the magnets in the presence of the sample. Samples of about 0.05 grams were tested which filled the test tube to a height of about 3 to 4 mm. The relative magnetic susceptibility was determined by dividing the change in weight of the magnets obtained by the gram of iron in the sample. The strength of the magnetic field in the area of the sample was about 240 oersteds. When so measured, the above composition had a relative magnetic susceptibility of about 4.4 grams per gram of iron. When samples of magnetite or $Fe_3I_4$ of laboratory grade obtained from three sources were tested as above, the relative magnetic susceptibilities obtained for the samples were in the range of 3.3 to 3.6 grams per gram of iron. A sample of substantially pure iron of standard of reference grade had a magnetic susceptibility of 2 grams per gram of iron.

The run as described above was repeated except that the amount of the ferrous sulfate hydrate added was increased to 10 grams and the amount of the caustic was also increased to 12.5 milliliters. After reaction for 2 hours on the steam bath and purification as described above, the product obtained contained 15.0 percent iron on an air-dried basis and had a relative magnetic susceptibility of 4.2 grams per gram of iron.

A third run was made where the procedure used above was followed except that 15 grams of ferrous sulfate and 18 milliliters of the caustic solution were reacted with the 10 grams of lignosulfonate. After reaction for 2 hours and purification, the composition obtained contained 19.1 percent iron on an air-dried basis and had a relative magnetic susceptibility of 6.1 grams per gram of iron.

In a manner similar to that above, ferrous chloride was reacted with the lignosulfonate and alkali in place of ferrous sulfate. Ferrous chloride was added in the same ratio as ferrus sulfate to supply about 2 grams of iron per 10 grams of the lignosulfonate. The product obtained contained 18.6 percent iron and had a relative magnetic susceptibility of 4.6 grams per gram of iron.

EXAMPLE II

The lignosulfonate of Example I was reacted with ferric sulfate in the preparation of a ferromagnetic composition.

The lignosulfonate in an amount of 10 grams was dissolved in 150 milliliters of distilled water placed in a 500-milliliter 3-neck flask. To this solution, 7.2 grams of ferric sulfate containing about 28 percent iron was added which thus supplied 2 grams of iron per the 10 grams of lignosulfonate. The lignosulfonate solution in the flask was purged with nitrogen before and after the addition of the ferric sulfate. The sodium hydroxide solution was likewise purged with nitrogen prior to the addition of 12 milliliters of the 6.2N caustic. The mixture, under the atmosphere of nitrogen, was then heated in a steam bath for 3 hours with the stirring after which an additional 6 milliliters of the nitrogen-scrubbed caustic was added and the reaction continued for 2 more hours. The sample was filtered and dialyzed. The dialyzate upon drying containing 17.2 percent iron and had a relative magnetic susceptibility of 1.3 grams per gram of iron.

A second run was made with ferric sulfate similar to that above except that the reaction was not carried out under a nitrogen atmosphere but stirred in an open beaker in a steam bath. The product obtained was not ferromagentic having a relative magnetic susceptibility of only 0.2 grams per gram of iron.

A third run was made similar to the first run where the reaction was carried out under a nitrogen atmosphere except that in place of ferric sulfate, 10 grams of ferrous sulfate heptahydrate were added to supply 2 grams of iron per 10 grams of the lignosulfonate. After the ferrous sulfate was dissolved in the lignosulfonate solution, the reaction mixture was adjusted to a pH of about 10 by the addition of 10 milliliters of 6.2N sodium hydroxide solution which had been previously scrubbed with nitrogen. The reaction mixture, under a nitrogen atmosphere in the flask, was placed in a steam bath and reacted with stirring for 6 hours. The addition of the caustic resulted in the formation of a gel-like precipitate in the reaction mixture, giving it a bluish-green color. The reaction mixture still retained the bluish-green color after reaction for 6 hours. The product was not ferromagnetic. However, a small sample was removed and placed in a 200-milliliter beaker. After the mixture was rapidly for about 30 minutes in the steam bath, the solution displayed ferromagnetic properties by being drawn toward a fixed magnet placed near the side of the beaker.

EXAMPLE III

The lignosulfonate fraction of Example I was also reacted with the ferrous sulfate hydrate under constant pH conditions.

In 150 milliliters of distilled water, 10 grams of the lignosulfonate were dissolved at room temperature after which 10 grams of ferrous sulfate heptahydrate were intermixed. After the iron sulfate was dissolved, the pH was adjusted to pH 7 by dropwise addition of 1.6N sodium hydroxide solution. The sample was then heated to about 90° C in a steam bath, and while being stirred, periodic additions of the sodium hydroxide solution were made to the reaction mixture to maintain the pH at about 7. A blue-green colored, gel-like precipitate appeared to be present, and as the reaction continued with the addition of caustic, the solution-suspension became darker and the precipitate dissolved. After 2 hours, the reaction mixture was a dark brown ferromagnetic but was allowed to remain in the steam bath for an additional half hour. A total of approximately 45 milliliters of caustic had been allowed. The sample was removed from the steam bath, allowed to cool to room temperature, and filtered. The filter cake, upon air-drying weighed 0.6 gram and was mainly calcium sulfate. The filtrate and the filter cake washings were combined and dialyzed in a regenerated cellulose dialysis casing against running water. The dialyzate was air-dried to give 13.3 grams of ferromagnetic composition. The composition contained 14.7 weight percent iron and had a relative magnetic susceptibility of 5.1 when measured as described in Example I above.

A second run was made where the reaction mixture was maintained at a pH of 6. The lignosulfonate used for this run was a lignosulfonate fraction obtained from a fermented calciumbase spent sulfite liquor by gel permeation. The fraction represented a 20 percent portion of the liquor and was an intermediate fraction having an average molecular weight of about 32,000 and a sulfonate sulfur content of 5.6 percent. Ten grams of the above lignsulfonate were dissolved in 150 milliliters of distilled water and reacted with 10 grams of the ferrous sulfate hydrate in a manner similar to that described above. After the ferrous sulfate had dissolved in the lignosulfonate solution, approximately 3 milliliters of the 1.6N sodium hydroxide solution were added to bring the pH of the reaction mixture to 6. The reaction mixture was placed in the steam bath and reacted at a temperature of about 91° C with periodic additions of the caustic solution being made. The caustic was fairly rapidly consumed for the first 20 to 30 minutes and thereafter at a decreasing rate. When the reaction was terminal after 3.25 hours, 46 milliliters of caustic had been added. The caustic was still being consumed but at a relatively slow rate. Upon cooling, the reacton mixture was filtered to give a filter cake of about 0.8 gram and then dialyzed. Upon drying of the dialyzate, 1.34 grams of ferromagnetic compositions were obtained which contained about 14.5 weight percent of iron on an air-dried basis. The relative magnetic susceptibility of the product, measured as described above, was 5.2.

A third run simiar to that immediately preceding above was made wherein the pH was maintained at 5. After heating for about 7.5 hours, only about 14 milliliters of the caustic had been consumed. Upon drying of the dialyzate, 11.3 grams of product were obtained which contained 8,9 weight percent iron. The composition, however, did not display magentic properties.

EXAMPLE IV

A ferromagnetic lignosulfonte was prepared using a multi-step process. A lignosulfonate fraction obtained by fractionation by gel permeation of a fermented calcium-base liquor which was base-exchanged to the sodium base was used. The lignosulfonate fraction had a weight average molecular weigth of about 35,000.

In 2.25 liters of distilled water, 150 grams of the lignosulfonate were dissolved with 150 grams of the ferrous sulfate hydrate. To the mixture, 180 milliliters of 6.2N sodium hydroxide were added and the mixture heated on a steam bath while being stirred for 4 hours. After cooling to room temperture, the product was filtered, dialyzed, and the dialyzate was then dried. The product contained 16.2 percent iron on an air-dried basis and had a relative magnetic susceptibility of 5.8 grams per gram of iron.

The above ferromagnetic composition in an amount of 10 grams was dissolved in 150 milliliters of water and treated with 10 grams of additional ferrous sulfate heptahydrate. After the ferrous sulfate hydrate was dissolved in the solution, 12 milliliters of 6.2N sodium hydroxide were added, and the mixture was reacted in a steam bath for 2 hours. After the reaction mixture was cooled to room temperature, it was filtered and dialyzed and the dialyzate dried. The composition obtained had 28.4 percent iron on an air-dried basis and had a relative magnetic susceptibility of 7.2 grams per gram of iron.

The composition containing 28.4 percent iron was reacted with additional ferrous sulfate. The composition was dissolved in 150 milliliters of water in the amount of 5 grams, and 5 grams of ferrous sulfate hydrate and 6 milliliters of 6.2N sodium hydroxide solution were added. The mixture was reacted in a steam bath for 2 hours. Upon filtration, dialysis, and drying of the dialyzate in the manner described above, the ferromagentic composition obtained contained about 33.4 percent iron on air-dried basis and was found to have a relative magentic susceptibility of about 6.9 grams per gram of iron.

EXAMPLE V

A series of runs was where the lignosulfonate of Example I was reacted with the ferrous sulfate hydrate using different amounts of alkali. In each run, a different amount of alkali or sodium hydroxide was added to the solution of 10 grams of the lignosulfate and 10 grams of the ferrous sulfate hydrate in 150 milliliters of distilled water. The samples were reacted in a steam bath at about 90° C for 2 hours after which the reaction mixtures were cooled to room temperature, filtered, dialyzed, the dialyzate dried, and the iron content and relative magnetic susceptibility determined.

The results are shown in the table below:

| Run No. | ml of 6.2N NaOH Added | % Iron in Product | Relative Magnetic Susceptibility of Product, g/g of Iron |
| --- | --- | --- | --- |
| 1 | 0 | 4.5 | 0 |
| 2 | 3 | 7.6 | 2.2 |
| 3 | 4 | 8.3 | 3.2 |
| 4 | 8 | 10.8 | 3.2 |
| 5 | 11 | 13.1 | 3.5 |
| 6 | 12 | 16.2 | 5.8 |

EXAMPLE VI

To show the effect of reaction time, the lignosulfonate fraction described in Example I was reacted with iron and caustic in a 3-neck round bottom flask from which samples were periodically withdrawn and the increase in weight of the sample was noted upon subjecting the liquid sample to a magnetic field.

The lignosulfonate in an amount of 10 grams was dissolved in 150 milliliters of distilled water placed in a 3-neck round bottom flask. After the lignosulfonate was dissolved, 10 grams of the ferrous sulfate hydrate were added and dissolved. To this mixture, 12 milliliters of 6.2N caustic were added and the flask, equipped with a stirrer and reflux condenser, was placed on a steam bath. As the reaction proceeded, samples in an amount of about 4 milliliters were periodically withdrawn over a period of 19 hours. An increase in weight of each of the liquid samples upon being subjected to a magnetic field was determined by positioning a 1-gram sample on a 1-pan balance above an electromagnet and an electric current passed through the magnet. The increase in weights of the one gram samples and the times at which the samples were withdrawn are shown in the table below.

| Reaction Time, Minutes | Increase in Weight, Gram |
| --- | --- |
| 0 | — |
| 27 | .003 |
| 62 | .017 |
| 92 | .038 |
| 122 | .041 |
| 152 | .045 |
| 182 | .044 |
| 1142 | .039 |

After the mixture had been reacted for 19 hours with periodic withdrawal of the samples, the reaction of the remaining mixture was continued until the total reaction time was 72 hours. The product was then cooled and purified as described above. It contained 15.5 percent iron on an air-dried basis and had a relative magnetic susceptibitlity of 4.6 grams per gram of iron.

EXAMPLE VII

To illustrate the effect of viscosity of the solution on the reaction rate, a series of runs was made where the reaction of lignosulfonate with the iron compound in the presence of alkali was carried out in solutions or mixtures of different concentrations.

The lignosulfonate of Examples I in an amount of 2 grams was dissolved in 150 milliliters of water after which 2 grams of ferrous sulfate hydrate were added. The alkali in an amount of 2.4 milliliters of 6.2N sodium hydroxide was then added and the mixture heated on a steam bath for 2 hours. After the 2-hour reaction time, the product was purified as described in examples above and air-dried. Additional runs were made repeating the procedure above except that 5, 15, 20, and 25 grams of lignosulfonate and the proportional amounts of other reactants were reacted in the 150 milliliters of distilled water. The reaction times for all the runs used were 2 hours except for the last run, made with 25 grams of lignosulfonate, which was increased to 3 hours to obtain a more complete reaction. As the concentration of the solution increased, the extent of reaction of the iron with the lignosulfonate decreased which is indicated by the decrease in the iron content in the final composition and also the decrease in the relative magnetic susceptibility. Increasing the reaction time from 2 hours to 3 hours for the last run showed an improvement.

| Amount of Reactants Added | | | % Iron in Composition | Relative Magnetic Susceptibility g/g of Iron |
| --- | --- | --- | --- | --- |
| Lignosulfonate Grams | Iron Salt Grams | Caustic ml 6.2N | | |
| 2 | 2 | 2.4 | 16.0 | 4.9 |
| 5 | 5 | 6.0 | 15.4 | 3.7 |
| 15 | 15 | 18.0 | 14.8 | 4.7 |
| 20 | 20 | 24.0 | 14.0 | 3.2 |
| 25 | 25 | 30.0 | 14.1 | 3.7 |

EXAMPLE VIII

The procedure for the preparation of a ferromagnetic iron lignosulfonate similar to that described in Example I was followed except that to the lignosulfonate fraction of Example I non-lignin constituents were added to show the effect of their presence. Sugars, arabinose and xylose, which are the main carbohydrates remaining in a fermented spent sulfite liquor, and sugar carboxylic acids were added in amounts normally found in fermented liquor. Sugar acids and lactones were extracted from a fermented clacium-base liquor and were subjected to alkaline hydrolysis to convert the lactones to acids. In the runs made, 10 grams of the lignosulfonate containing the non-lignin constituents in various amounts were dissoled in 150 milliliters of water and reacted with 10 grams of ferrous sulfate heptahydrate with the addition of 12 milliliters of 6.2N sodium hydroxide. The reaction was carried out in a steam bath for 2 hours after which the reaction mixture was filtered and the filtrate obtained analyzed to determine the amount of iron in the filtrate. Substantially all of the iron found in the filtrate remains with the dialyzate after dialysis so that the iron content of the filtrate is indicative of the total iron which will be in the final product.

The details of the experiment and the results obtained are given in the table below.

| Sugar and Sugar Acid Content of Lignosulfonate, Weight % | | | Total Iron in Filtrate, Grams | % Iron in Product | Relative Magnetic Susceptibility, g/g of Iron |
| --- | --- | --- | --- | --- | --- |
| Arabinose | Xylose | Acids | | | |
| 0   | 0   | 0   | 1.88 | 15.4 | 3.9 |
| 2.4 | —   | —   | 1.34 | 13.3 | 3.1 |
| —   | 3.6 | —   | 1.39 | 13.3 | 3.0 |
| —   | 7.2 | —   | 0.96 | 12.6 | 0.6 |
| —   | —   | 2.0 | 1.37 | 14.8 | 1.1 |
| —   | —   | 4.0 | 1.24 | 13.8 | 0.7 |
| 2.4 | 3.6 | —   | 1.04 | 12.0 | 1.1 |
| 2.4 | 3.6 | 2.0 | 0.94 | 12.7 | 0.1 |

EXAMPLE IX

Low molecular weight and other lignosulfonates were used in the preparation of ferromagnetic iron lignosulfonates.

An unfermented calcium-base liquor was fractionated by gel permeation to remove the high molecular weight lignosulfonates. The fraction obtained represented 55 percent of the low molecular weight portion of the spent sulfite liquor, which included the sugars and other low molecular weight constituents. The fraction contained 37.3 percent by weight of reducing substance expressed as sugars. The lignosulfonate was recovered from this fraction by amine salt purification. The fraction was treated with triamylamine under acid conditions resulting in the formation of the triamylammonium lignosulfonate which was extracted from the solution by use of n-butanol. The butanol phase was washed with water to remove the water-soluble non-lignin constituents and the triamylammonium lignosulfonate was then converted to sodium base by treatment of the butanol solution with sodium hydroxide. The sodium lignosulfonate obtained had a diffusion coefficient of 13.1, indicating that the average molecular weight of the lignosulfonate was about 8000. The sulfonte sulfur content was 5.6 percent.

The above low molecular weight lignosulfonate was reacted with ferrous sulfate in a manner similar to that described above. The grams of the lignosulfonate were dissolved in 150 milliliters of water in an open vessel. The ferrous sulfate hydrate in an amount of 10 grams was then dissolved after which 12 milliliters of 6.2N sodium hydroxide solution were added and the mixture reacted in a steam bath for 2 hours with agitation in open air. After purification in a manner similar to that described in examples above, the composition obtained contained 19.5 percent iron on an air-dried basis and has a relative magnetic susceptibility of 5.9 grams per gram of iron. A ferromagnetic lignosulfonate was also obtained by reaction of the iron compound and alkali with a vanillin raffinate.

In preparation of vanillin, lignosulfonate is subjected to an alkaline air oxidation in presence of a metallic catalyst. In the oxidation, the lignin is subjected to considerable cleavage so that the product remaining is a somewhat modified low molecular weight lignosulfonate. The vanillin raffinate used had a diffusion coefficient of 23.8, which indicated that the average molecular weight of the lignosulfonate was in the range of 1,800 to 2,000.

In addition, runs were made with lignosulfonates obtained by different means.

A calcium-base fermented spent sulfite liquor was converted to the sodium base by precipitation of the calcium as calcium sulfate upon addition of sodium sulfate. The base-exchanged liquor was then oxidized with hydrogen peroxide. When the oxidized liquor was used in preparation of the iron lignosulfonate, the product obtained was not ferromagnetic. However, upon dialysis of a portion of the oxidized liquor and repeating the run, the composition obtained contained 18.6 percent iron on an oven-dried basis and had a relative magnetic susceptibility of about 5 grams per gram of iron.

A lignosulfonate obtained on dialysis of a spent sulfite liquor was also used. A fermented calcium-base liquor converted to a sodium lignosulfonate by addition of sodium sulfate to precipitate the calcium was dialyzed for 2 days against running tap water. The dialyzed lignosulfonate obtained has a diffusion coefficient of 11.2, indicating that the average molecular weight of the lignosulfonate was around 13,000 and close to the average molecular weight of a fermented calcium-base liquor. Upon reaction in a manner similar to that above, the product obtained contained 18.0 percent iron on an air dry basis and has a relative magnetic susceptibility of 8.5 grams per gram of iron.

A triamylammonium lignosulfonate obtained upon purification of a spent sulfite liquor was also reacted in a manner similar to that above. The triamylamine salt was insoluble in water. However, upon addition of the caustic the amine was regenerated and a sodium lignosulfonate was formed, which dissolved in the solution. The product obtained contained 17.6 percent iron on an air dry basis and had a relative magnetic susceptibility of 2.9 grams per gram of iron.

A lignosulfonate recovered by acid precipitation was also used. A fermented calcium-base spent sulfite liquor was converted to the sodium base and subjected to a severe alkaline treatment. The alkaline treatment comprised the addition of about 45 percent sodium hydroxide as a 50 percent solution to a 50 weight percent solution of the sodium-base liquor and heating the mixture at a temperature of 155° C for about 2 hours. The lignosulfonate was recovered from the reaction product by acidification with sulfuric acid to precipitate the lignosulfonate. It had a sulfonate sulfur content of 1.7 weight percent. Upon reaction of the lignosulfonate, the iron lignosulfonate composition obtained contained about 17.5 percent iron on an oven-dried basis and had a relative magnetic susceptibility of 2.4 grams per gram of iron.

Likewise, a lignosulfonate obtained upon sulfonation of kraft lignin was used. The sulfonated kraft lignin contained about 4.3 percent sulfonate sulfur and when reacted in a manner similar to that described above, gave an iron lignosulfonate composition which contained 18.8 percent iron and had a relative magnetic susceptibility of 3.6 grams per gram of iron.

EXAMPLE X

A ferromagnetic iron lignosulfonate was prepared at temperatures requiring pressure equipment.

A lignosulfonate fraction having an average molecular weight of around 32,000 was reacted with the ferrous sulfate hydrate and alkali at a temperature of 150° C. The lignosulfonate in an amount of 10 grams was dissolved in 180 milliliters of water. Ferrous sulfate in the amount of 10 grams was added to the solution after which the 12 milliliters of 6.2N sodium hydroxide were added. The mixture was placed in a sealed container having a volume of about 800 milliliters and rotated in an oven at a temperature of 150° C for 2 hours. After purification in a manner similar to that described above, the product obtained contained 16 percent iron and had a relative magnetic susceptibility of 2.9 grams per gram of iron.

EXAMPLE XI

A fermented calcium-base liquor which was not treated to remove the low molecular weight non-lignin constituents was reacted with ferrous sulfate and alkali in a manner similar to that described above. Two grams of the spent sulfite liquor solids were dissolved in 60 milliliters of distilled water in a 400-milliliter beaker. After the addition of the ferrous sulfate hydrate in an amount of 2 grams and of 2.4 milliliters of the 6.2N sodium hydroxide solution, the reaction mixture was placed in the steam bath and reacted for 2 hours. The product upon cooling was filtered, and the filtrate obtained was divided in two equal fractions. One-half of the filtrate was purified by dialysis and upon air drying of the dialyzate, 0.7 grams of product were obtained. The product contained 14.9 percent iron and had a relative magnetic susceptibility of 0.03 grams per gram of iron.

To the second half of the filtrate, 3.5 additional grams of the ferrous sulfate hydrate were dissolved and 3.4 milliliters of the caustic added. The mixture was reacted in the steam bath with stirring in air for 2 hours. After purification, 1.1 grams of the product were obtained. The product contained 24.9 percent iron and had a relative magnetic susceptibility of 2.7 grams per gram of iron.

EXAMPLE XII

A ferromagnetic lignosulfonate was prepared and tested as a micronutrient.

A sample of fermented calcium-base liquor was processed by continuous dialysis through a polyvinyl alcohol membrane and the dialyzate was concentrated and converted to the sodium-base by addition of sodium sulfate. Precipitated calcium sulfate was removed by filtration and the filtrate was adjusted to pH 11 with 5 percent caustic.

A sample of this basified sodium-base liquor (100 g. solids) was oxidized by the addition of 20 milliliters of 30 weight percent hydrogen peroxide and heating the mixture for 60 hours at 35–40° C. The product obtained was acidified to pH 2 with 6N hydrochloric acid then dialyzed against running tap water for 72 hours using a regenerated cellulose casing.

A portion of the dialyzate from above, containing 23.4 grams solids dissolved in 773 milliliters of water, was adjusted to pH 4 by addition of a small amount of 18 percent sodium hydroxide solution after which 40.0 grams of ferrous sulfate heptahydrate were added, resulting in the pH dropping to the range of 3 to 3.5. The pH of the mixture was adjusted to pH 4 by addition of the 18 percent sodium hydroxide solution and heated at 45° C for 30 minutes on a water bath before further additions of caustic were made to bring the pH to 8. At pH 8, the reaction mixture was heated for about 30 minutes after which the pH was increased to 10 and heated or digested at 80° C for an additional 15 hours. The reaction mixture after cooling was centrifuged and filtered to remove the insolubles and the filtrate obtained was dialyzed against running water in a regenerated cellulose casting to remove the soluble inorganics. After dialysis for about 72 hours, the dialyzate had a ph of 5 to 6 and was air-dried. The product had iron content of 18.4 percent iron and a relative magnetic susceptibility of 5.7.

The above product was tested as a micronutrient to see whether it was effective in supplying iron to plants. The effectiveness of the product was compared to known iron micronutrients, including an iron complex of ethylenediamine di-o-hydroxyphenylacetic acid and an iron lignosulfonate sold under the trademark of Iron KE-MIN. The Iron KE-MIN was manufactured by addition of 10.1 percent iron to a fermented calcium-base spent sulfite liquor and the product digested at a temperature from 80° to 90° C at a pH of 4 or so.

In the test made, a soil known to be deficient in iron was treated with reagent chemicals to provide the required nitrogen, phosphorus and potash content, and the iron compound was added in a sufficient amount to supply 20 ppm iron. Each soil was then potted and five seeds of a hybrid sorghum were planted. In each of the runs made with the particular micronutrient, three pots were used as well as a control of an equal number of plants. The pots were intermixed at random and placed under controlled ultraviolet conditions.

After 16 days, the control and the pots containing the magnetic iron lignosulfonate showed signs of iron chlorosis while the plants which were treated with 20 ppm iron supplied as Iron KE-MIN and a like amount of the iron supplied as the ethylenediamine di-o-hydroxyphenylacetic acid complex were green, showing that the products were effective for this use. No correction for the iron deficiency was obtained with the magnetic lignosulfonate after 48 days with severe chlorosis being evident.

EXAMPLE XIII

A ferromagnetic lignosulfonate composition was prepared at room temperature.

Ferrous sulfate heptahydrate in an amount of 1 grams was added to a solution of 10 grams sodium lignosulfonate in 200 ml of water in a vessel at room temperature. After the ferrous sulfate was dissolved, 25 ml of 2.9 N sodium hydroxide solution was slowly added to the reaction mixture. The vessel was loosely sealed by placing a cover on the vessel to limit the exposure of the reaction mixture to air as it was very slowly stirred. The reaction mixture indicated ferromagnetic properties after 5 hours of reaction, but the reaction was continued for an additional 15 hours to insure more complete reaction. After centrifugation to remove small amounts of insolubles, the mixture was air dried to obtain a product which contained 10.2% iron. The relative magnetic susceptibility of the product was 3.9 grams per gram of iron which was equivalent to about 2.1 grams per gram of iron.

A second run was made similar to that above except that instead of covering the open vessel to limit the rate of oxidation, air was bubbled through the reaction mixture. The product obtained had a relative magnetic susceptibility of 0.2 grams per gram of iron.

EXAMPLE XIV

A ferromagnetic lignosulfonate was prepared by addition of a mixture of ferrous and ferric salts in the preparation of the ferromagnetic lignosulfonate composition.

Twenty grams of a sodium lignosulfonate was dissolved in 150 ml of water through which nitrogen was continually bubbled to minimize presence of oxygen in the reacting atmosphere. The solution was heated to 90° C and 6.6 grams of ferrous sulfate heptahydrate was dissolved in the solution followed by the addition of 11.8 grams of ferric sulfate. The pH of the reaction mixture was raised to 7 by the addition of 6 N sodium hydroxide solution and maintained at pH 7 for 2½ hours while the solution was heated at 90° C. The solution was cooled to room temperature under a nitrogen atmosphere and ten centrifuged. A portion of the solution after centrifugation was air dried and the remainder of the solution was dialyzed to remove the inorganic salts prior to air drying. The non-dialyzed, air-dried product obtained contained 10.3% iron and had a relative susceptibility of 4.1 grams per gram of iron, while the dialyzed product free of the inorganic salts contained 16.8% iron which had a relative magnetic susceptibility of 4 grams per gram of iron.

A second run similar to that described above was made where the ferrous and ferric iron were added to the solution in equal amounts and the reaction carried out with oxidation. Ferric sulfate in an amount of 9.5 grams and ferrous sulfate heptahydrate in an amount of 10 grams were dissolved in a solution containing 20 grams of sodium lignosulfonate in 150 ml of water. The mixture was reaced at 90° C at pH 7 for 2½ hours with air being bubbled through the mixture. The air-dried non-dialyzed product obtained contained 10.6% iron and had a relative magnetic susceptibility of 5.8 grams per gram of iron. The air-dried product of the portion of the sample which was dialyzed contained 16.8% iron and had a relative magnetic susceptibility of 6.5 grams per gram of iron.

EXAMPLE XV

A ferromagnetic lignosulfonate was prepared containing nickel and iron. To a solution containing 10 grams of sodium lignosulfonate in 150 ml of water, nickel chloride in an amount representing 0.6 grams of nickel was added. After the nickel chloride had dissolved, 7 grams of ferrous sulfate heptahydrate which represented 1.4 grams of iron was dissolved after which 25 ml of 2.8 N sodium hydroxide solution was added. The open reaction vessel was covered to limit the contact of air with the reaction mixture. The reaction mixture was slowly stirred at room temperature for a period of 5 days after which it was centrifuged and the solution obtained dialyzed against running water for 24 hours and air dried. The air-dried product contained 8.7% iron and 4.4% nickel. The relative magnetic susceptibility of the product was 1.9 grams per gram of metal.

EXAMPLE XVI

A ferromagnetic lignosulfonate was prepared containing iron and manganese.

In a solution containing 10 grams of sodium lignosulfonate in 125 ml of water, 8.4 grams of ferrous sulfate heptahydrate was dissolved at 80° C. The solution was heated to 90° C after which potassium permanganate solution containing 0.86 grams potassium permanganate in 75 ml of water was added dropwise to the hot stirred mixture over a period of 15 minutes. With the addition of the potassium permanganate, a sodium hydroxide solution containing 2.8 grams sodium hydroxide in 40 ml of water was also added to maintain the pH of the reaction mixture between pH 5.9 and 6.1 during the addition of the potassium permanganate and after the addition of the permanganate at a ph of about 7. The open reaction vessel was loosely covered and the reaction continued at 90° C for 2½ hours with constant stirring. After the reaction mixture was cooled to room temperature, the reaction mixture was centrifuged and the solution obtained dialyzed and air dried. The air-dried product contained 13.2% iron and 1.8% manganese and had a relative magnetic susceptibility of 2.3 grams per gram of metal.

A second run was made where 7.0 grams of ferrous sulfate heptahydrate and 1.84 grams of manganese sulfate monohydrate were dissolved in a solution containing 1 grams of sodium lignosulfonate in 150 ml of water. After the ferrous and magnanese salts were dissolved, 2.8 grams of sodium hydroxide dissolved in 50 ml of water was added slowly while stirring the mixture. The reaction mixture was maintained at room temperature for 24 hours with constant stirring after which it was heated to 90° C and vigorously stirred for 6 hours. The reaction mixture was cooled to room temperature, centrifuged and dialyzed. The solution remaining after dialysis was air dried to give a product containing 11% iron and 3.8% manganese. The relative magnetic susceptibility of the air-dried product was 2.8 grams per gram of iron.

EXAMPLE XVII

A sulfonated tannin was used for the preparation of a ferromagnetic composition.

A sulfonated tannin obtained by sulfonation of hemlock bark under alkaline conditions was dialyzed against running water for four days to obtain about a 60% fraction of the higher molecular weight constituents of the sulfonated tannin. The fraction was air dried to obtain a product which contained 3.8% sulfonate sulfur.

In a solution containing 10 grams of the dialyzed sulfonate tannin in 200 ml of water, 4.7 grams of ferric sulfate containing 22.6% iron and 5 grams of ferrous sulfate heptahydrate were dissolved. After the iron salts were dissolved, 3.7 grams of sodium hydroxide was added and the mixture reacted over night at about 85° C by placing the reaction vessel on a water bath. After the reaction, the mixture was cooled, centrifuged and the solution remaining air dried. The air-dried product contained 4.9% iron and had a relative magnetic susceptibility of 101 grams per gram of iron.

We claim:

1. A composition comprising a material selected from the group consisting of lignosulfonate and sulfonated tannin combined with iron, said composition being ferromagnetic.

2. The composition of claim 1 wherein said iron is present in a structure form of an iron oxide.

3. The composition of claim 2 wherein said structural form comprises that of gamma ferric oxide.

4. The composition of claim 2 wherein said structure form of iron comprises that of magnetite.

5. Ferromagnetic lignosulfonate.

6. Ferromagnetic iron lignosulfonate.

7. Ferromagnetic sulfonated tannin.

8. Ferromagnetic iron sulfonated tannin.

9. The composition of claim 1 wherein said composition also contains a metal selected from the group consisting of nickel and manganese.

10. The composition of claim 1 wherein said material has been rendered water insoluble by reaction with a phenolformaldehyde resin.

11. A process for the preparation of ferromagnetic composition, which comprises dissolving an iron compound and a material selected from the group consisting of lignosulfonate and sulfonated tannin in an aqueous medium and mixing the mixture in the presence of an alkali at a temperature up to 230° C at a pH of at least about 5.5 to form a ferromagnetic composition, said iron compound being dissolved in an amount of at least twice the stoichiometric amount, as ferric iron, to react with the sulfonate groups of the material, said mixture being heated under conditions to obtain the iron in the ferrous and ferric states, and said material being substantially free of polyhydroxy, polycarboxy, and lactone-type non-lignin constitutents having molecular weight less than about 400.

12. A process according to claim 11 wherein the mixture is heated at a pH of at least 6 until from 0.9 to 1.5 equivalents of alkali per equivalent of iron are reacted and the lignosulfonate or sulfonated tannin concentration in the solution is from 0.5 to 20 weight percent.

13. A process according to claim 12 wherein the iron compound is a water-soluble inorganic iron salt and the material is a lignosulfonate fraction of a residual pulping liquor.

14. A process according to claim 12 wherein the iron salt is dissolved in the solution in an amount to supply from 10 to 40 weight percent iron, based upon the lignosulfonate or sulfonated tannin, and the mixture heated until about 1 equivalent of the alkali per equivalent of iron is reacted with the iron salt and lignosulfonate or sulfonated tannin.

15. A process according to claim 13 wherein the lignosulfonate is a lignosulfonate fraction of a spent sulfite liquor containing less than 5 weight percent sugars and sugar acids with the sugar acid content not exceeding 2 weight percent.

16. A process according to claim 12 wherein the mixture is heated at a temperature in the range of 90° to 140° C at a pH in the range of 7 to 10 in the presence of sodium hydroxide, and the iron salt is a ferrous salt.

17. A process according to claim 16 wherein the water-soluble ferrous salt is a ferrous sulfate added in an amount to supply from 20 to 40 weight percent iron and the mixture is heated at a temperature in te range of 90° to 100° C with agitation in air to oxidize the iron from ferrous to ferric states.

18. A process according to claim 12 wherein said iron is added as a mixture of ferrous and ferric compounds.

19. The process of claim 18 wherein said ferric and ferrous compounds are present in proportions suitable for the formation of a magnetic iron oxide.

20. A process for the preparation of a ferromagnetic composition, which comprises dissolving a water-soluble iron salt and a material selected from the group consisting of a lignosulfonate and sulfonated tannin in water in an amount to obtain up to 30 weight percent of the material and at least 9 weight percent iron, based upon the weight of the material, adding from 0.9 to 1.5 equivalents of an alkali metal hydroxide per equivalent of iron to the solution, and heating the mixture at a temperature in the range of 40° to 230° C for from 0.5 to 24 hours to react the iron with the material to form a ferromagnetic composition, said material being substantially free of organic constituents having molecular weights less than 400, and said mixture being heated with the iron being in ferrous and ferric states.

21. A process according to claim 20 wherein the water-soluble iron salt is an inorganic salt and is added in an amount of from 20 to 50 weight percent, and the material is at a concentration of from 3 to 10 weight percent in the solution.

22. A process according to claim 21 wherein the mixture is a lignosulfonate fraction of a spent sulfite pulping liquor and the mixture is heated in the presence of sodium hydroxide at a temperature in the range of 90° to 140° C for from ¼ to 4 hours.

23. A process according to claim 22 wherein the iron salt is ferrous sulfate and the mixture is heated in the presence of air to oxidize a portion of the iron from ferrous to ferric state.

24. A process according to claim 21 wherein the material is a sulfonated tannin and the mixture is heated in the presence of sodium hydroxide at a temperature in the range of 90° to 140° C for from ¼ to 4 hours.

25. A process according to claim 24 wherein the iron salt is ferrous sulfate and the mixture is heated in the presence of air to oxidize a portion of the iron from ferrous to ferric state.

26. A composition comprising a material selected from the group consisting of lignosulfonate and sulfonated tannin combined with iron, said composition having a relative magnetic susceptability, when measured in a magnetic field of 240 oersteds, based upon the iron content thereof, is at least 60% of substantially pure iron.

27. The composition of claim 26 wherein said material is lignosulfonate.

28. The composition of claim 26 wherein said material is sulfonated tannin.

29. The composition of claim 26 wherein said iron is present in a structural form of an iron oxide.

30. The composition of claim 29 wherein said structural form comprises that of gamma ferric oxide.

31. The composition of claim 29 wherein said structural form of iron comprises that of magnetite.

* * * * *

UNITED STATES PATENT OFFICE
CERTIFICATE OF CORRECTION

Patent No. 4,019,995          Dated April 26, 1977

Inventor(s) William Scott Briggs et al.

It is certified that error appears in the above-identified patent and that said Letters Patent are hereby corrected as shown below:

Column 3, line 50, capitalize "a".

Column 7, line 10, before the word "recovery", change "of" to "or"; line 28, change "sulfonate" to "sulfonates".

Column 10, line 38, after the word "lignosulfonate", insert -- and iron --.

Column 12, line 20, change "0.05" to "0.015"; line 24, change "gram" to "grams"; line 29, change "$Fe_3I_4$" to "$Fe_3O_4$"; line 54, change "ferrus" to "ferrous".

Column 13, line 6, delete "the"; line 10, change "containing" to "contained"; line 59, after the word "brown", insert -- and --; line 62, change "allowed" to "added".

Column 16, line 27, change "Examples" to "Example".

Column 17, line 8, change "dissoled" to "dissolved"; lines 59-60 change "sulfonte" to "sulfonate"; line 63, change "The" to "Ten".

Column 18, line 4, change "has" to "had".

UNITED STATES PATENT OFFICE
CERTIFICATE OF CORRECTION

Patent No. 4,019,995  Dated April 26, 1977

Inventor(s) William Scott Briggs et al.

It is certified that error appears in the above-identified patent and that said Letters Patent are hereby corrected as shown below:

Column 21, line 29, change "ten" to "then".

Column 22, line 32, change "1 grams" to "10 grams"; line 67, change "101 grams" to "1.1 grams".

Column 24, line 1, change "te" to "the".

Signed and Sealed this thirtieth Day of August 1977

[SEAL]

Attest:

RUTH C. MASON
*Attesting Officer*

C. MARSHALL DANN
*Commissioner of Patents and Trademarks*